US006951610B2

(12) United States Patent
Leonard et al.

(10) Patent No.: US 6,951,610 B2
(45) Date of Patent: Oct. 4, 2005

(54) METHOD AND DEVICE FOR PRODUCING AQUEOUS IODINE AND OTHER HALOGEN SOLUTIONS

(76) Inventors: John Alex Leonard, 56 Coral Harbour Crescent, Thornhill, Ontario (CA), L3T 2Z7; Maurice Tinkler, 118 Melrose Ave., King City, Ontario (CA), L7B 1J6

( * ) Notice: Subject to any disclaimer, the term of this patent is extended or adjusted under 35 U.S.C. 154(b) by 160 days.

(21) Appl. No.: 10/059,577

(22) Filed: Jan. 29, 2002

(65) Prior Publication Data

US 2003/0141249 A1 Jul. 31, 2003

(51) Int. Cl.[7] ............................................. C02F 1/76
(52) U.S. Cl. .................... 210/206; 210/501; 210/502.1; 210/634; 210/638; 210/644; 210/640
(58) Field of Search ................. 210/206, 501, 210/502.1, 634, 638, 644, 640, 650, 651, 205, 198.1, 753, 500.22, 507; 423/500

(56) References Cited

U.S. PATENT DOCUMENTS

| 3,408,295 | A | 10/1968 | Vaichulis |
| 4,384,960 | A | 5/1983 | Polley |
| 4,483,771 | A | * 11/1984 | Koch .......................... 210/490 |
| 5,275,736 | A | 1/1994 | O'Dowd |
| 5,853,574 | A | 12/1998 | Harvey et al. |

OTHER PUBLICATIONS

The Pharmacological Basis for Therapeutics, 5th edition, L.S. Goodman and A. Gilman, Chapter 67, "Thyroid and Anti–thyroid drugs".
Use of Iodine Disinfection, J.Am, Water Works Assn., vol. 57, 1965.
Disinfection, Sterilization and Preservation, fifth edition Ed. Seymour S. Block, Chapter 8, Iodine and Iodine Compounds, W. Gottardi.
European Applied Research Reports: Nuclear Science and Technology, 1985, 6, 631, "A review of the aqueous chemistry and partitioning of inorganic iodine under LWR severe accident conditions".
The Thyroid and Iodine, 8, E. Roti, L.E. Braverman.

* cited by examiner

Primary Examiner—W. L. Walker
Assistant Examiner—Krishnan S Menon
(74) Attorney, Agent, or Firm—Fay, Sharpe, Fagan, Minnich & McKee, LLP (57) ABSTRACT

Method and devices for producing aqueous iodine and other halogen solutions for dietary, disinfection, sterilization and preservation purposes and the uses thereof.

19 Claims, 4 Drawing Sheets

METHOD AND DEVICE FOR PRODUCING AQUEOUS IODINE AND OTHER HALOGEN SOLUTIONS

TECHNICAL FIELD

The invention refers to the production of aqueous solutions of pure elemental iodine and the iodine-containing species therein, and of the equivalent liquid or solutions of other halogens.

BACKGROUND OF THE INVENTION

Iodine, in the form of Lugol's solution or tincture of iodine, has long been recognized as an effective biocide. Compounded iodine in the form of an iodophor has also been noted for these biocidal properties since 1960. Biocide properties of iodine have been documented since at least as early as 1830.

Iodine is an essential element in the body for bio-activity in humans, animals and birds, aquatic animals and fish, and in plant life. For example, iodine is essential for the function of the thyroid in human beings (The Pharmacological Basis for Therapeutics, 5th edition, L. S. Goodman and A. Gilman, Chapter 67, "Thyroid and Anti-thyroid drugs") and necessitates an adequate daily intake of iodine, typically 150 micrograms for an adult. Without normal amounts of iodine, the thyroid-stimulating hormone (TSH or thyrotropin) no longer properly stimulates and controls the thyroid-releasing hormone thyroxine. Thyroxine, an amino acid of the thyroid gland, contains iodine. If the thyroxine is excreted in excess, the thyroid hypertrophies and the body's metabolism is stimulated in an undesirable manner. This condition, hyperthyroidism, manifests itself in over-activity of the thyroid gland. Another consequence of iodine deficiency in the diet is the possible contraction of hypothyroidism, i.e. underactivity of the thyroid gland, which results in slowing down the body's metabolism and causing goitre and mental deficiencies.

Many parts of the world, especially former glaciated areas, are deficient in dietary iodine. The richest sources of dietary iodine are those derived from marine life. Seafish contain 200 to 1000 micrograms/kg and shellfish a similar amount. To obtain the recommended level of 150 microgram daily, a standard adult human requirement, one would have to eat 5 kg of vegetables or 3 kg of meat or freshwater fish. To promote iodine sufficiency, iodine is provided as a dietary supplement in many countries by addition of iodate to table salt, typically at a level of 100 micrograms/gram of salt.

A major potential use of aqueous iodine solutions is in disinfection, sterilization and preservation of food stuffs and feed stuffs. There is a growing concern about bacterial, viral and protozoal contamination of ingredients for human foods and finished human food products. Bacteria of major concern include Salmonella, Typhinium, *Staphylococcus Aureus, Vibrio Cholera, Bacillus Anthracis* and certain strains of *E. Coli*. Examples of viruses are poliomyelitis and influenza. Examples of protozoa are *Giardia, Chlamydomonas* and *Entamoeba*.

While the disinfecting, sterilizing and preserving properties of dilute aqueous iodine solutions have been known for at least a century, the use with food ingredients, food stuffs, feed ingredients and feeds has been very limited apart from the notable case of iodized salt consumption by humans and animals. The reasons for the lack of application have been several fold:

a) It was believed that high concentrations (30 mg/L or higher) were needed to be effective. At these levels there is distinct coloration of the solution and a strong iodine taste when added to products.

b) It was difficult to prepare dilute aqueous iodine solutions in a controllable manner in an industrial environment. A further impediment was that the techniques used often resulted in solutions contaminated with solid iodine or iodine compounds which were considered a health risk.

A number of patents and other publications have recorded different approaches to producing solutions of iodine in water. These range from the classical iodine saturator as discussed in Black A. P. et al., "Use of Iodine for disinfection", J. Am. Water Works Assn., Vol. 57, 1965 and later variants of this design to the use of iodine complexes such as iodophors (Disinfection, Sterilization and Preservation, Fifth edition, Ed. Seymour S. Block, Chapter 8, "Iodine and Iodine Compounds", W. Gottardi), and to dispersing iodine vapor through a barrier material. These mechanical or chemical approaches met with varying degrees of success and presented various restrictions in use. With respect to dissolving crystalline iodine in water, mechanical methods had problems with respect to particle carry-over and the use of iodine in admixture with other chemicals presented limitations on control of iodine concentration and introduced issues of contamination by other components of the formulation.

Vaichulis (U.S. Pat. No. 3,408,295) describes an apparatus and method for disinfecting or purifying water that relies on the flow of water to be treated through a bed of elemental iodine and the consequent formation of an iodine-containing solution. The aqueous solution passes through a porous body, such as a fritted glass disc, which has a porosity such that it is pervious to the passage of a water solution of iodine therethrough and impervious to the passage of iodine in undissolved form.

Polley (U.S. Pat. No. 4,384,960) shows that elemental iodine can be retained by several means inside a container and can be dissolved to form an aqueous iodine solution by expelling water from inside the container through the body of iodine. Only one of these means is claimed, being the placing of solid elemental iodine in a removable dropper tip of the container. Retention of solid iodine is provided for by materials that are porous or otherwise pervious to water but have perforations or openings therein sufficiently small to retain undissolved iodine.

Neither of these patents anticipates the practical use of the transfer of iodine vapor to produce aqueous iodine solutions nor do they adequately show how solid iodine is retained yet water flow is permitted.

The O'Dowd patent (U.S. Pat. No. 5,275,736) uses a non-porous, iodine-solving, solid barrier identified as a plastic material to enclose crystalline iodine which is permeable to diffusion of iodine vapor from the inside to the exterior medium where it can act as a disinfectant. The patent refers in particular to the use of Lugol's solution, tincture of iodine and an iodophor as the source of iodine. It was emphasized that these solutions contain a low percentage of available iodine. In addition, an iodophor, a complex of iodine, was selected to limit the rate of transfer of iodine. This method was intended to prevent the contamination of the exterior medium, provide for sustained replenishment of iodine in the exterior medium as it is consumed, and produce an aqueous iodine solution which is biocidal, yet without the physical disadvantages of common iodine-containing formulations. The patent identifies four plastic materials that can be used for the iodine-solving barrier: linear polyethylene, isotactic polyethylene, polyoxymethylene and polybutylene terephthalate. In practice, these permit only very low rates of transfer of iodine that are impractical for common use.

There are two explanations for this type of behavior. Firstly, the patent describes the rate and extent of transfer of iodine as being dependent on the relative vapor pressures of iodine on either side of the barrier as well as the physicochemical nature of the barrier material. Over time, a balancing of these vapor pressures would take place such that the final concentration in the receiving medium would be directly related to the vapor pressure within the barrier. However, in reality, the rate of this vapor diffusion process is determined by the "Law of Mass Action" (Guldberg and Waage, 1864) with the rate of reaction dependent upon the molecular concentrations of the reactants, i.e. $I_2$ and $H_2O$, and the products. It is not surprising therefore that the observed rates of transfer are low and decline with time. Secondly, the examples of the solid barriers provided in this patent may be subject to poisoning which would reduce their effectiveness in use. Consequently, the process of iodine vapor transfer as described in the O'Dowd patent is exceedingly slow and is impractical for application to useful devices.

By contrast, the inventors of the methods, devices and uses of the current patent have focused on practical designs for generating iodine solutions. They use solid elemental iodine and other iodine compounds and have avoided the use of complexing agents such as are typical of iodophor formulations. In particular, they select porous, vapor-permeable membranes to enclose the iodine source and this combination has the distinct advantage of much higher transfer rates than the use of solid plastic materials described in the prior art.

The product of this invention, an essentially saturated aqueous solution of iodine, contains what is known as thermodynamically free iodine. This form of iodine is not complexed and is totally available chemically. According to Clough, (European Applied Research Reports: Nuclear Science and Technology, 1985, 6, 631, "A review of the aqueous chemistry and partitioning of inorganic iodine under LWR severe accident conditions"), elemental iodine ($I_2$) reacts in aqueous solution to give numerous products in various proportions dependent on pH, temperature and iodine concentration. These include the dissociated, hydrolyzed forms of iodic acid (HI) and higher polyiodides, periodic acid (HOI), iodate ($IO^{3-}$) and species such as $OI^-$, $HI_2O^{2-}$, $I_2O^{2-}$ and $H_2OI^+$. Of these, the major bactericidal species are $I_2$ and its solvated species, $I_2.H_2O$ and $I_2H.OH$, HOI and iodine cation $H_2OI^+$ (which is only effective at a pH<1). Iodide ($I^-$) (except that which is in hydrolysis equilibrium with HOI) and iodate ($IO^{3-}$) are not germicidal. Highly diluted solutions ($10^{-5}$ Mol/L or 2.54 mg/L) for potable or swimming pool water do not form iodates in the presence of iodide below a pH of 8.

SUMMARY OF THE INVENTION

It is the object of this invention to define a simple, efficient and practical method for producing aqueous iodine solutions without admixture with particles of solid iodine; to apply similar techniques to the production of aqueous solutions of other halogens; to produce devices based on this method; and to apply such devices for dietary, disinfection, sterilization and preservation purposes and for the many uses thereof which have been described in the published literature.

A method of producing an aqueous solution of thermodynamically free iodine from iodine vapor transferred across a membrane from an iodine source calls for selecting a membrane that is permeable to iodine and water vapor but is impermeable to liquids and solids. The membrane is provided in the form of an enclosure that contains a source of iodine vapor. A vessel contains a medium which may be liquid such as water or an inert gas i.e. a gas that does not react with iodine and which receives the iodine vapor that permeates across the membrane.

An iodine vapor-permeable membrane is sealed into a sachet or pouch that contains an iodine source. The sachet or pouch is contained in an iodine-receiving medium inside a vessel in which the flow of the receiving medium is controlled. Means for supplying agitation, temperature control, and pressure control are also provided. A means for removing a volume of iodine solution is also provided.

The invention uses vapor-permeable, organic or inorganic, solid or liquid membranes chosen for their special properties which permit high transfer rates of iodine vapor without the transfer of solid iodine and which resist significant ingress of the external liquid medium. The iodine source is encapsulated in the membrane and generates vapor which passes through the membrane to be absorbed in a static or flowing liquid or inert gas which does not complex with iodine. The membrane pouch or sachet is located within a container or cartridge which contains the flowing or static receiving medium. An iodine solution thus prepared may be discharged from the container or cartridge in either a batch or continuous mode. In the case where the medium is an inert gas, the mixture of iodine vapor and inert gas may be conducted into a liquid to form a liquid iodine solution of the required strength. An alternative method is to strip iodine vapor by means of an inert gas in either a batch or continuous mode from the liquid iodine solution issuing from the container or cartridge and to conduct the iodine vapor and inert gas mixture into a liquid to form an iodine solution of the desired strength. An iodine solution prepared by any of these methods may be diluted continuously, batchwise, manually or mechanically to produce a working-strength solution which may be used for dietary, disinfecting, sterilizing and preservation purposes.

Significant elements of this invention are described as follows. It is understood that, where technically feasible, the same points of argument are extended to the use of other halogens in place of iodine.

a) the selection of the iodine source;

b) the selection of membranes permeable to iodine vapor, but not to liquids or solids;

c) the encapsulation of the iodine source in said membrane;

d) locating the encapsulated sources, herein referred to as pouches or sachets, in a container or cartridge;

e) selecting a material for the container or cartridge that is substantially impervious and non-reactive to iodine vapor and iodine solutions;

f) designing the container or cartridge containing the pouches or sachets in such a manner that there is a maximum exposure of active membrane area, i.e. area which separates the iodine source from the receiving medium in the container or cartridge;

g) designing a control system such that flow in and out of the container or cartridge containing the aqueous iodine solution of desired strength can be regulated to yield the desired flow rate in either a batch or continuous mode and h) providing a control system for regulating temperature and pressure of the receiving medium.

Research performed during the development of the methods and devices of this invention (to determine the selection of the iodine vapor source) showed that for high vapor transfer rates (this was typically measured in mg. of iodine transmitted per hour per square meter of membrane area in contact with both the iodine source and the receiving medium), the source of the iodine vapor would ideally be crystalline iodine, ground crystalline iodine and ground crystalline iodine mixed with inert solids, such as sand. These transfer rates are dependent upon the nature of the membrane and on the temperature and pressure of the receiving medium, be it a liquid or a mixture of liquid and gas surrounding the membrane. If lower vapor transfer rates are desired or acceptable, complexed iodophors, neat or diluted, may be used as the source of iodine vapor, if compatible with the membrane material.

This invention required the selection of a membrane that would permit the transfer of iodine vapor but would prevent the transmission of solid iodine or iodine compounds or liquid formulations containing iodine or iodine compounds. The necessity for non-transmission of these, except for the iodine vapor, is based on the need to control the iodine concentration in the receiving medium and to protect against known toxicity effects of these sources.

Examples of these iodine vapor-permeable membranes are permeable fabrics, reverse osmosis membranes, fuel cell membranes, diafiltration and ultrafiltration membranes, molecular sieves, nano-porous filters and media, and microcrystalline filters.

In practice, the pore size of suitable membranes needs to be chosen to be compatible with the defined requirements of use. In order to permit the transfer of iodine vapor and to restrict passage of solid iodine, the pore size should be no greater than 5 microns. The pore density (pores per unit area) can be chosen at will. Iodine transfer will be enhanced by higher pore density membranes but practical considerations of membrane strength and the requirements of durability in use will impose an upper limit on acceptable pore densities. To prevent ingress of the external medium into the interior of the sachet or pouch, it is preferable that the membrane is hydrophobic.

As to the physical form of the membranes, they may be single film or laminates or combinations of both. A further important consideration of membrane selection is the physical strength of the membrane. Adequate strength is needed to assure that the pouch or sachet is physically strong enough to safely contain the iodine source without leaking. Also this strength is needed to assure that the pouches or sachets may be produced using standard plastic-forming machinery such as pressure heat sealers, infra-red sealers and induction sealers. Thus it may be necessary to reinforce the membrane material by means of "open weave" layers of polymeric materials. Also the membrane material may be ribbed for reinforcement purposes. These reinforcements may be needed for certain devices of this invention for the purpose of adding strength and rigidity to the pouches or sachets. A further purpose is to assist the flow of the receiving medium in an optimum manner, e.g. to aid in the mass transfer of the iodine vapor into the receiving medium. In addition, these reinforcements may improve the production of the pouches or sachets The materials selected for the container or cartridge used in the devices of this invention must meet the following criteria:

a) They must be impermeable to iodine vapor or iodine solutions, and b) They must be practically non-reactive with the iodine solution produced.

It is often feasible to use commercially available containers or cartridges originally designed for other applications such as flow-through filters, for the purpose of containing pouches or sachets filled with the iodine source.

The flow of the medium in and out of the container or cartridge is controlled. Liquid moving devices such as pumps and valves may be used for the liquid and gas inlets to the container in conjunction with liquid moving devices or valves for the liquid or gas outlet of the container. This same control system may also sustain a desired recycle rate of the receiving medium through the container or cartridge to permit blending to produce a working strength solution. A feed-back control from a colorimetric absorption instrument has also proven successful in controlling the final solution strength.

A control system for temperature and pressure acts in conjunction with the above control system. The addition of an immersion heater or immersion cartridge provides a means of controlling the temperature of the receiving medium. The liquid moving devices and the valves in the inlet and outlet lines may be manipulated in such a manner that not only the flow is controlled, but also the pressure in the receiving container.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
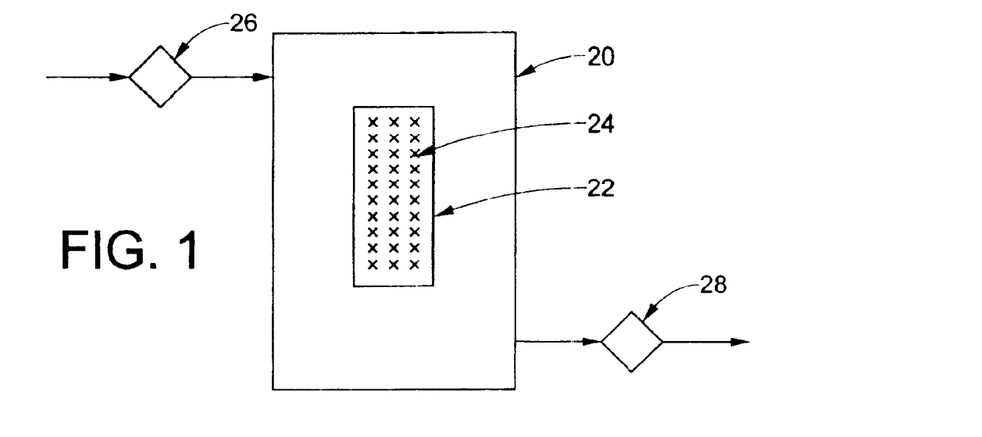
FIG. 1 shows a typical device representative of the invention.

Referring now to the drawings wherein the showings are for the purposes of illustrating the preferred embodiment of the invention only and not for purposes of limiting same, FIG. 1 shows a typical device representative of the invention.

In FIG. 1, a container 20 fabricated from a material substantially impervious to iodine vapors or aqueous iodine solution contains a hermetically sealed pouch or sachet 22 which in turn is fabricated from a membrane material which is permeable to iodine vapors only. The pouch or sachet 22 is filled with solid crystalline iodine, mixtures of solid crystalline iodine and inert solids or with iodine compounds in liquid or solid form. The iodine source is designated as 24 in this drawing.

A pump or other pressure source and a valve or a combination of both, designated as 26, control the liquid flow into the container 20. A valve 28 controls the outflow of the aqueous iodine solution. The device can be operated in a batch mode using element 26 to introduce the liquid with valve 28 closed. Valve 28 can be operated once the desirable iodine concentration is reached within the container 20 to draw out the solution. Alternately, the device can be operated in a continuous mode with element 26 and valve 28 controlling the flow through the system.

In the case that an inert gas is used to carry the iodine vapors out of the device, a blower or other gas pressure source combined with element 26 control the flow of gas into the container 20. A blower and/or a valve control the outflow of the iodine vapor-containing inert gas. As described above, the device can be operated in a batch or continuous mode by manipulating pressure source and/or valve 26 and valve 28.

Figure 2:
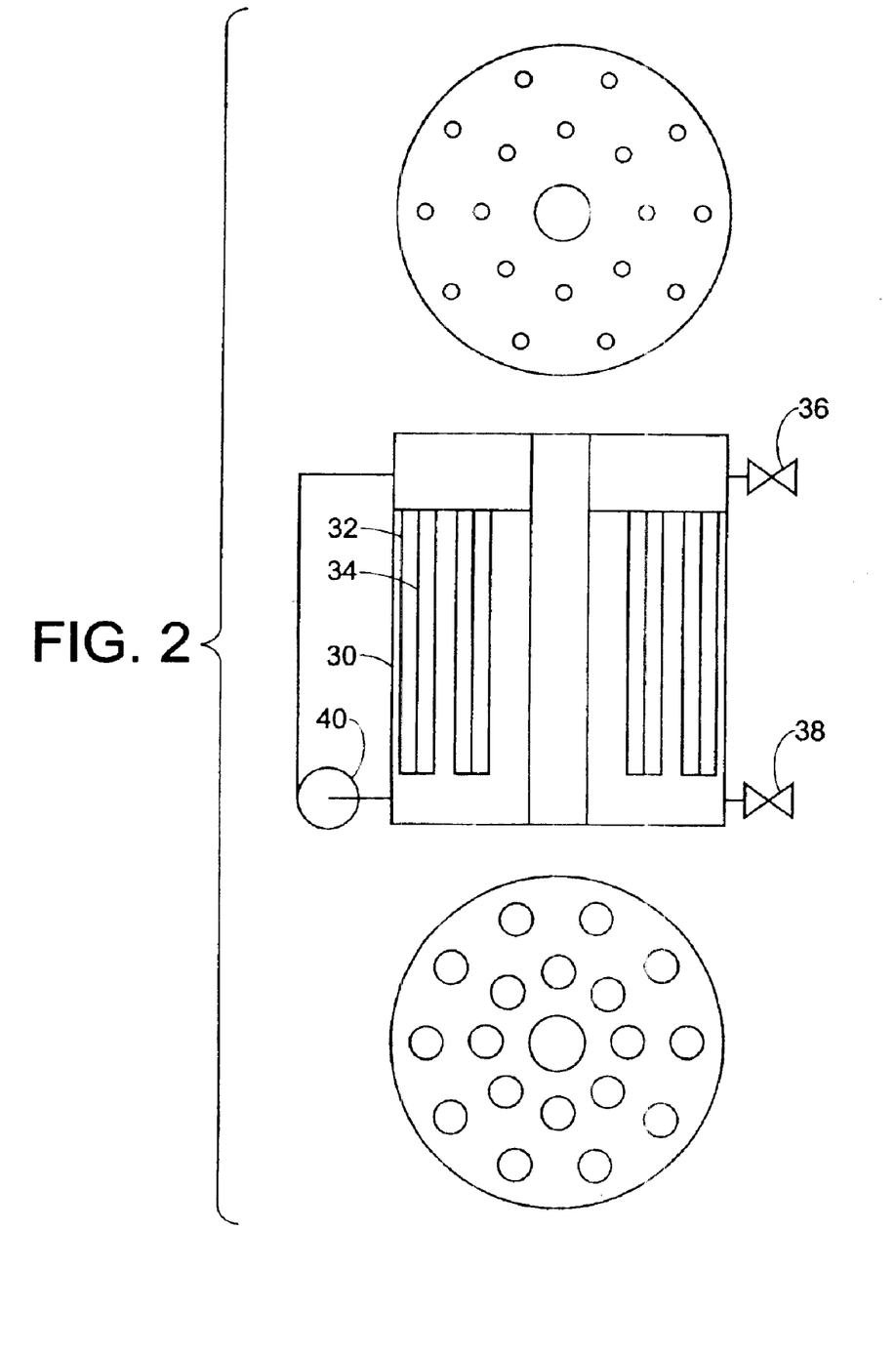
FIG. 2 shows a typical device which may be used for industrial purposes.

Turning now to FIG. 2, this embodiment shows a typical device which may be used for industrial purposes. The container 30 which again is fabricated from a material substantially impervious to iodine vapors or aqueous iodine solutions, contains a multiplicity of hermetically sealed pouches, cartridges or sachets 30 which in turn are fabricated from a membrane material which is permeable to iodine vapors. These pouches or sachets 32 are filled with solid crystalline iodine or mixtures of solid crystalline iodine and an inert solid, i.e. a solid not reactive with the iodine component, or with liquid formulations containing iodine or iodine compounds. The filling point of these pouches or sachets is designated 34.

An inlet 36 introduces water or inert gas into container 30. An outlet 38 controls the outflow of iodine vapor-laden inert gas or of an aqueous iodine solution. The temperature of the receiving medium inside the container 30 may be controlled by a heating device such as a cartridge heater (not shown). A circulation pump 40 may be used to equilibrate the temperature and the iodine concentration inside the container 30 and to promote better iodine mass transfer within it.

The device can be operated in a batch mode using inlet 36 to introduce the liquid with outlet 38 closed. Outlet 38 can be opened once the desirable concentration of iodine is reached within the container 30 to draw out the solution. Alternately, the device can be operated in a continuous mode with inlet 36 and outlet 38 controlling the flow through the container 30.

Figure 3:
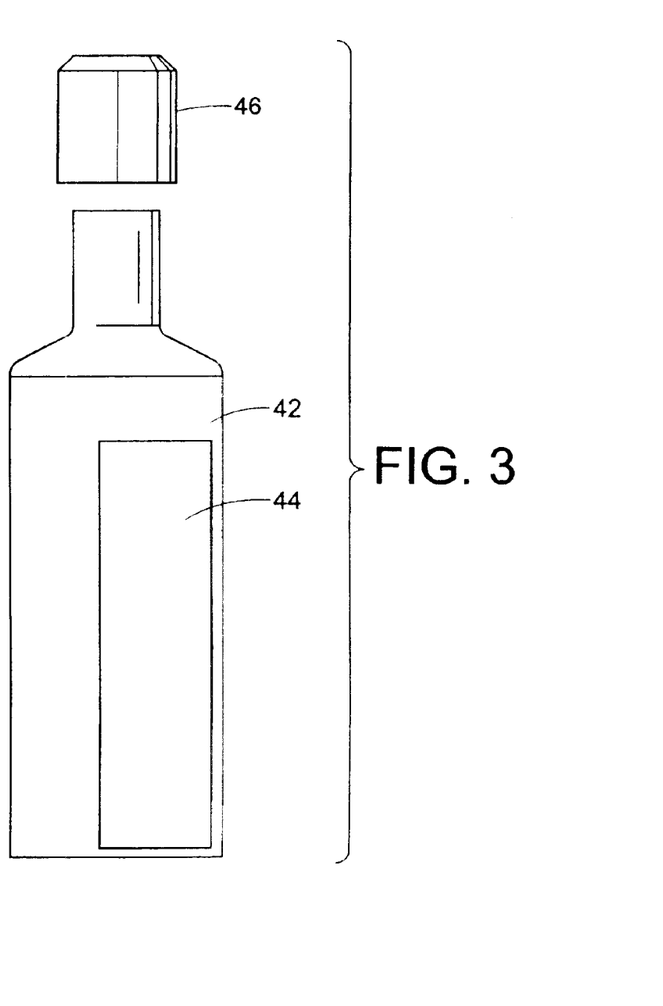
FIG. 3 shows an iodine generator for preparing small batches of aqueous iodine solutions.

The next selected embodiment, FIG. 3, shows an iodine generator for preparing small batches of aqueous iodine solutions. A bottle container 42 made from a material substantially impervious to iodine vapors and aqueous iodine solutions contains a hermetically sealed iodine generator pouch 44 which, in turn, is made from a membrane material which is permeable to iodine vapor only. The iodine generator pouch 44 is filled with solid crystalline iodine or with a mixture of solid crystalline iodine and an inert solid or with liquid formulations containing iodine or iodine compounds.

The bottle container 42 is filled with water and then sealed with a closure cap or dispensing cap 46 to contain the solution and to prevent the escape of iodine vapors. Subsequent to filling and sealing of the container 42 a saturation concentration of iodine is reached within the bottle container 42 during a time span experimentally established by the inventors. Once the batch within the container 42 reaches the saturation concentration of iodine, part or all of the liquid may be removed by using the closure or dispensing cap 46. The liquid may be used as such or be diluted to the desired strength. The bottle can be refilled with clean water until all iodine is consumed.

Figure 4:
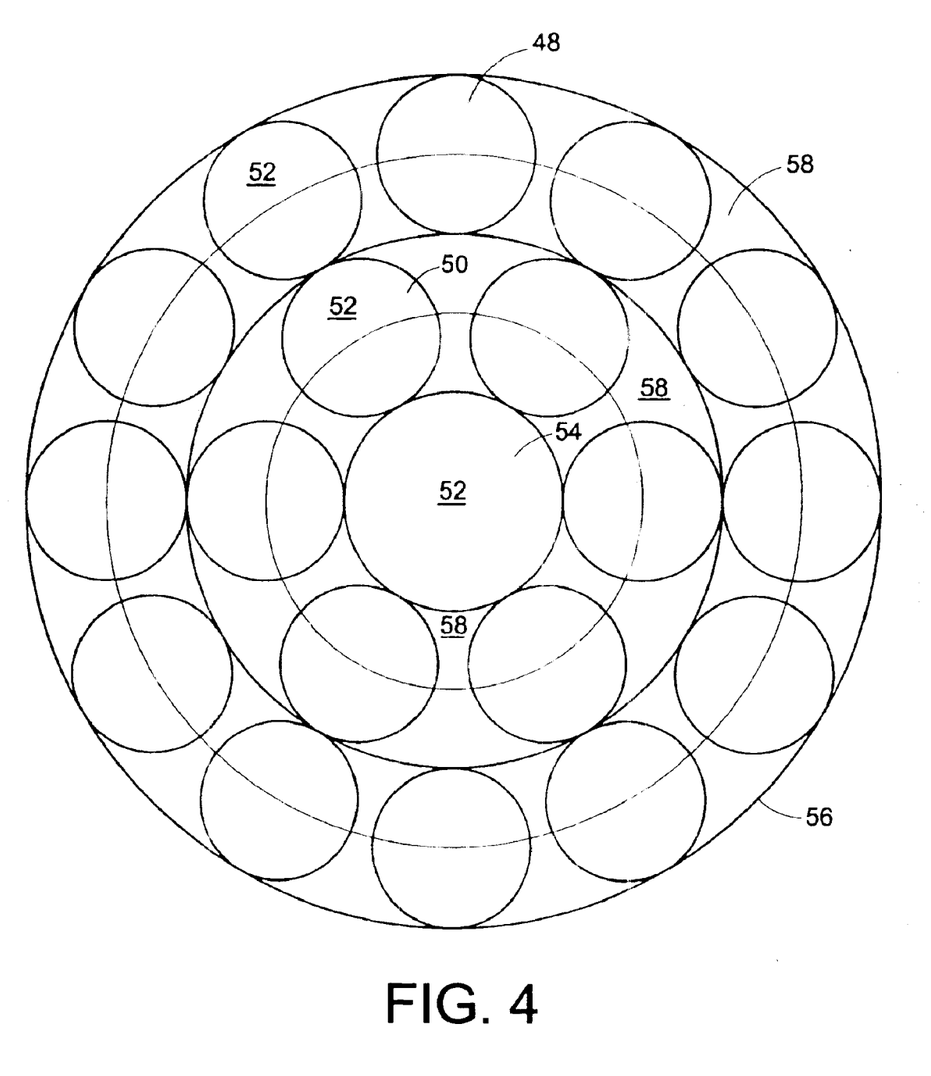
FIG. 4 shows a typical cross-section perpendicular to the pouches or sachets of a container or cartridge containing a multiplicity of pouches or sachets.

FIG. 4 is another selected embodiment showing a typical cross-section perpendicular to the pouches or sachets of a container or cartridge containing a multiplicity of pouches or sachets. Items 48 and 50 represent the individual sachets, a twelve array and a six array, respectively. Each sachet is filled at 52 with either pure, ground crystalline iodine or a mixture (typically 50/50 percent) of ground crystalline iodine and an inert solid such as sand, and may contain a supporting frame to facilitate the filling operation and to maintain the shape of the sachet or pouch during use. The center sachet 54 is also filled with fill 52. Item 56 is the shell of the container or cartridge which contains the sachets 48, 50 and 54 and the receiving medium enclosed in and/or flowing through the passages. The objective is to maximize the surface area of the iodine charged yet leave an ample void space between to permit good contact with the surrounding absorbent liquid.

Each sachet in the above arrays may be of different or equal length to increase the quantity of iodine source contained in same. Also two or more multiple arrays as described may be stacked in a single container to again increase the quantity of iodine source contained therein. A random arrangement may also function well if transfer rates are limited by a formal layout.

Figure 5:
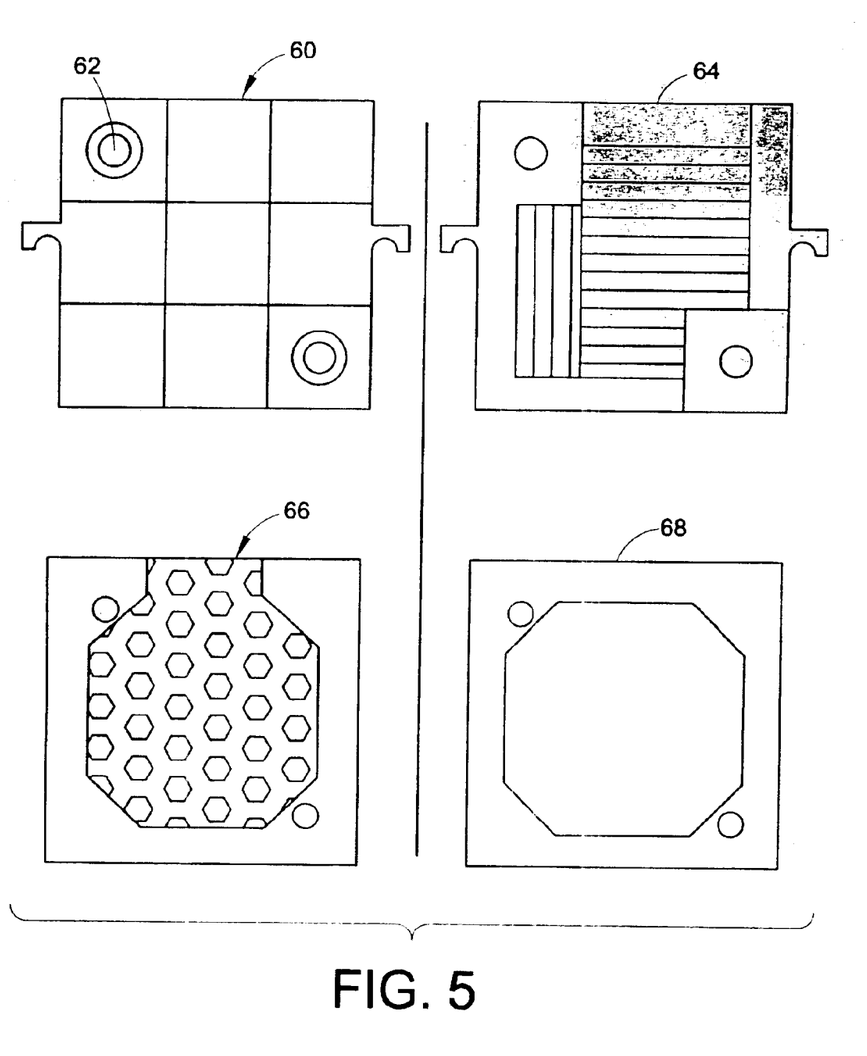
FIG. 5 shows the elements of a plate & frame prototype iodine generator for use in circulated systems.

Finally, FIG. 5 shows the four key elements of a plate & frame prototype iodine generator for use in circulated systems. The unit shown is a converted pilot scale chamber filter type press which comprises a back plate 60 with mounting studs and bolt holes 62 and a front plate which would normally hold sets of chamber or press plates 64 and filter papers between them. The assembly is held together by bolts which compress the package of these plates and filter papers.

For this device, the filter medium is replaced by a custom designed iodine sachet 66 which is filled with a weighed iodine charge and top sealed, and a flexible plastic frame 68 to contain the center section of the sachet. Drainage holes are cut in the corners of sachet 66 and frame 68 to permit circulation and drainage from the chamber area.

The press plate 64 is double-sided and ribbed to facilitate liquid flow across the face of the plate and has circular channels joining the drainage holes and connected by drainage channels to the face. Assembly of a four sachet module starts with the back mounting plate 62, frame 68, sachet 66, press plate 64 followed by 68; 66; 64; 68; 66; 64; 68; 66; 64 and finally, outer plate 60. Support bolts and studs compress the module. As the plastic frames and the outer part of the iodine sachet are flexible, they can be compressed to prevent leakage.

A circulating system is connected to the lower connection and the absorbing liquid is pumped through it and the air displaced to discharge from the upper connection. The unit can be used as a single pass or recirculating system as required.

In practice, the temperature of the receiving medium is in the range of about −10 to 110 degrees Centigrade. The pressure ranges from vacuum to about 5 atmospheres.

The invention has been described with reference to preferred embodiments, in particular with reference to the use of iodine. Similar techniques to those provided by this invention are applicable to the other halogens but such use may require different conditions according to the chemistry of the halogen in question. Obviously, modifications and alterations will occur to others skilled in the art upon reading and understanding these specifications. It is the intention of the inventors to include all such modifications and alterations insofar as they come within the scope of the appended claims or equivalents thereof.

What is claimed is:

1. A method of producing an aqueous solution of thermodynamically free iodine from iodine vapor transferred across a porous membrane from an iodine source, comprising the following steps:
   selecting a porous membrane that is permeable to iodine and water vapor but impermeable to liquids and solids;
   providing a source of iodine vapor;
   providing such membrane in the form of an enclosure to contain the source of iodine vapor;
   providing a vessel that contains a receiving medium for the iodine vapor; and
   permeating iodine vapor across the membrane.

2. The method of claim 1 wherein the iodine source is iodine as an iodine-releasing solid or an iodine-releasing liquid that contains iodine in solution or in a complex form.

3. The method of claim 2 including the additional steps of:
   absorbing the iodine vapor in the liquid contained in the vessel;
   mixing the iodine vapor with inert gas contained in or flowing through the vessel; and
   controlling flow of the receiving medium such that it is either static or moving.

4. The method of claim 3 including the additional step of:
   passing the inert gas containing iodine vapor through a liquid medium that absorbs said iodine vapor.

5. The method of claim 1 wherein the iodine vapor-permeable membrane is an organic plastic material.

6. The method of claim 1 wherein the iodine vapor-permeable membrane is an inorganic material.

7. The method of claim 1 wherein the iodine vapor-permeable membrane is single ply.

8. The method of claim 1 wherein the iodine vapor-permeable membrane is multi-ply construction wherein the plies are of the same or different composition and structure.

9. The method of claim 1 wherein the iodine vapor-permeable membrane is a continuous film.

10. The method of claim 1 wherein the iodine vapor-permeable membrane is non-woven.

11. The method of claim 1 wherein the iodine vapor-permeable membrane is a nanostructure.

12. The method of claim 1 wherein the iodine vapor-permeable membrane is perforated.

13. The method of claim 1 wherein the membrane material is substantially non-permeable to solid iodine.

14. The method of claim 13, including the additional step of;
   transferring iodine vapor through discrete pores in the membrane of less than 5 microns.

15. The method of claim 1, including the additional steps of:
   providing a vessel of a material that is substantially impermeable to iodine vapor and essentially unreactive towards iodine;
   maintaining a temperature of the receiving medium in the range of about −10 to 110 degrees Centigrade;
   maintaining a pressure in the vessel containing the receiving medium in a range from vacuum to about 5 atmospheres; and
   constructing and testing the vessel for the specified pressure rating.

16. A method of preparing an iodine fluid for dietary purposes directly or by blending, comprising the steps of:
   selecting a porous membrane that is permeable to iodine and water vapor but impermeable to liquids and solids;
   providing such membrane in the form of an enclosure to contain the source of iodine vapor;
   providing a source of iodine vapor within the enclosure;
   providing a vessel that contains a receiving medium for the iodine vapor;
   controlling a flow of the iodine-receiving medium in the vessel;
   removing a measured volume of iodine solution from the vessel in a batch or continuous mode; and
   preparing an iodine fluid for dietary purposes.

17. A method of preparing a fluid for disinfecting, sterilizing and preserving food ingredients, food stuffs, feed ingredients and feedstuffs, comprising the steps of:
   selecting a porous membrane that is permeable to iodine and water vapor but impermeable to liquids and solids;
   providing such membrane in the form of an enclosure to contain the source of iodine vapor;
   providing a source of iodine vapor within the enclosure;
   providing a vessel that contains a receiving medium for the iodine vapor;
   removing a measured volume of iodine solution from the vessel in a batch or continuous mode; and
   preparing a fluid for disinfecting, sterilizing and preserving food ingredients, food stuffs, feed ingredients and feedstuffs.

18. A method for producing an aqueous solution of a halogen or mixture of halogens, comprising the steps of:
   selecting a porous membrane that is permeable to halogen and water vapor but impermeable to liquids and solids;
   providing such membrane in the form of an enclosure to contain the source of halogen vapor;
   providing a source of halogen vapor within the enclosure; and providing a vessel that contains a receiving medium for the halogen vapor.

19. The method of claim 18 including the additional steps of:
   absorbing the halogen vapor in the liquid contained in the vessel; mixing the halogen vapor with inert gas contained in or flowing through the vessel; and
   controlling flow of the receiving medium such that it is either static or moving.

* * * * *

UNITED STATES PATENT AND TRADEMARK OFFICE
CERTIFICATE OF CORRECTION

PATENT NO. : 6,951,610 B2
DATED : October 4, 2005
INVENTOR(S) : Tinkler et al.

It is certified that error appears in the above-identified patent and that said Letters Patent is hereby corrected as shown below:

<u>Title page,</u>
Item [12], should read:
-- Tinkler et al. --.
Item [75] Inventors, should read
-- Maurice Tinkler, 118 Melrose Ave., King City, Ontario (CA), L7B 1J6;
  John Alex Leonard, 56 Coral Harbour Crescent, Thornhill, Ontario
  (CA), L3T 2Z7 --.

Signed and Sealed this

Fourth Day of April, 2006

JON W. DUDAS
*Director of the United States Patent and Trademark Office*